US010575766B2

(12) United States Patent
Sato

(10) Patent No.: US 10,575,766 B2
(45) Date of Patent: Mar. 3, 2020

(54) MEASUREMENT DEVICE, MEASUREMENT METHOD, PROGRAM, AND RECORDING MEDIUM

(71) Applicant: Sony Corporation, Tokyo (JP)

(72) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 192 days.

(21) Appl. No.: 15/127,432

(22) PCT Filed: Feb. 9, 2015

(86) PCT No.: PCT/JP2015/053558
§ 371 (c)(1),
(2) Date: Sep. 20, 2016

(87) PCT Pub. No.: WO2015/151586
PCT Pub. Date: Oct. 8, 2015

(65) Prior Publication Data
US 2018/0168496 A1   Jun. 21, 2018

(30) Foreign Application Priority Data

Mar. 31, 2014   (JP) ................................. 2014-073674

(51) Int. Cl.
*A61B 5/1455* (2006.01)
*A61B 5/00* (2006.01)
(Continued)

(52) U.S. Cl.
CPC ........ *A61B 5/14558* (2013.01); *A61B 5/0075* (2013.01); *A61B 5/1455* (2013.01);
(Continued)

(58) Field of Classification Search
CPC ...... A61B 5/0059–0091; A61B 5/0261; A61B 5/14532; A61B 5/1455–1464; A61B 2562/0238
See application file for complete search history.

(56) References Cited

U.S. PATENT DOCUMENTS 5,331,958 A * 7/1994 Oppenheimer .... A61B 5/14535
356/39
5,962,852 A * 10/1999 Knuettel ............. A61B 5/0066
250/339.11
(Continued)

FOREIGN PATENT DOCUMENTS

JP   2008-203234 A   9/2008
JP   2011-087907 A   5/2011
(Continued)

OTHER PUBLICATIONS

International Search Report and Written Opinion and English translation thereof dated May 19, 2015 in connection with International Application No. PCT/JP2015/053558.
(Continued)

*Primary Examiner* — Catherine B Kuhlman
(74) *Attorney, Agent, or Firm* — Wolf, Greenfield & Sacks, P.C.

(57) ABSTRACT

[Object] To measure a form of light scattering in a body more simply.
[Solution] A measurement device according to the present disclosure includes: a light source configured to emit at least one kind of measurement light belonging to a predetermined wavelength band toward a measurement region formed by at least a part of a living body; a detection unit configured such that a plurality of sensors are arranged regularly in a predetermined disposition and the measurement light emitted from the light source and transmitted through the living body is detected by the plurality of sensors; and an analysis
(Continued)

unit configured to analyze at least one of rectilinearity of the measurement light in the living body and an optical distance from the light source using a detection result of the measurement light detected by the detection unit.

12 Claims, 10 Drawing Sheets

(51) Int. Cl.
 *A61B 5/145* (2006.01)
 *A61B 5/024* (2006.01)
(52) U.S. Cl.
 CPC ...... *A61B 5/14532* (2013.01); *A61B 5/14552* (2013.01); *A61B 5/02416* (2013.01); *A61B 2562/0238* (2013.01)

(56) References Cited

U.S. PATENT DOCUMENTS

| | | | |
|---|---|---|---|
| 8,749,620 | B1 | 6/2014 | Knight et al. |
| 2002/0084417 | A1 | 7/2002 | Khalil et al. |
| 2003/0023151 | A1 | 1/2003 | Khalil et al. |
| 2006/0089548 | A1 | 4/2006 | Hogan |
| 2008/0316323 | A1 | 12/2008 | Morita et al. |
| 2010/0292578 | A1 | 11/2010 | Sato |
| 2011/0276276 | A1 | 11/2011 | Kashyap et al. |
| 2012/0101347 | A1 | 4/2012 | Amano et al. |
| 2014/0316224 | A1 | 10/2014 | Sato |
| 2014/0323831 | A1* | 10/2014 | Sato .................... A61B 5/14552 600/301 |
| 2014/0343383 | A1 | 11/2014 | Sato |
| 2014/0350365 | A1* | 11/2014 | Sato .................... A61B 5/14532 600/324 |
| 2014/0364707 | A1 | 12/2014 | Kintz et al. |
| 2016/0091496 | A1 | 3/2016 | Xu et al. |
| 2017/0135616 | A1 | 5/2017 | Sato |

FOREIGN PATENT DOCUMENTS

| | | |
|---|---|---|
| JP | 2013-103094 A | 5/2013 |
| JP | 2013-121420 A | 6/2013 |
| JP | 2013-126510 A | 6/2013 |

OTHER PUBLICATIONS

International Preliminary Report on Patentability and English translation thereof dated Oct. 13, 2016 in connection with International Application No. PCT/JP2015/053558.
International Search Report and Written opinion and English translation thereof dated May 19, 2015 in connection with International Application No. PCT/JP2015/053561.
International Preliminary Report on Patentability and English translation thereof dated Oct. 13, 2016 in connection with International Application No. PCT/JP2015/053561.

* cited by examiner $$A(\lambda) = \sum_i A_i(\lambda) + G(\lambda) = \sum_i \varepsilon_i(\lambda) C_i l_i(\lambda) + G(\lambda)$$

$$A_i(\lambda) = \sum_j \varepsilon_{ij}(\lambda) C_{ij} l_i(\lambda)$$

MEASUREMENT DEVICE, MEASUREMENT METHOD, PROGRAM, AND RECORDING MEDIUM

CROSS-REFERENCE TO RELATED APPLICATIONS

This application is a National Stage of International Application No. PCT/JP2015/053558, filed in the Japanese Patent Office as a Receiving office on Feb. 9, 2015, which claims priority to Japanese Patent Application Number 2014-073674, filed in the Japanese Patent Office on Mar. 31, 2014, each of which is hereby incorporated by reference in its entirety.

TECHNICAL FIELD

The present disclosure relates to a measurement device, a measurement method, a program and a recording medium.

BACKGROUND ART

With recent increases in health concerns, requests for performing simple measurement of information regarding one's physical conditions without visiting a medical institution have increased. Specifically, requests for performing simple measurement of the concentrations of one's body fluid (for example, blood) components or the condition of one's pulse have increased.

To meet such requests, for example, various measurement devices measuring glucose concentrations in blood have been proposed. Examples of a method of measuring a glucose concentration include a method of measuring a spectral distribution or light intensity using optical characteristics such as light absorption or Raman spectroscopy and a method of measuring a change in light scattering using the fact that a scattering coefficient of a living body tissue changes due to a change in a glucose concentration in blood.

For example, the following Patent Literature 1 proposes a technology for using the fact that a scattering coefficient of a living body tissue changes due to a change in a glucose concentration in blood and estimating a blood glucose level by causing near infrared light to be incident on a living body tissue and measuring a scattering coefficient.

CITATION LIST

Patent Literature

Patent Literature 1: JP 2006-122579A

SUMMARY OF INVENTION

Technical Problem

In the method disclosed in the foregoing Patent Literature 1, however, a form of light scattering in a body may not be ascertained since a change in a glucose concentration is measured based on light intensity of an amount of rectilinear light received by one sensor.

The present disclosure is devised in view of the circumstances described above, for example, and it is desirable to provide a measurement device, a measurement method, a program, and a recording medium capable of more simply measuring a form of light scattering in a body.

Solution to Problem

According to the present disclosure, there is provided a measurement device including: a light source configured to emit at least one kind of measurement light belonging to a predetermined wavelength band toward a measurement region formed by at least a part of a living body; a detection unit configured such that a plurality of sensors are arranged regularly in a predetermined disposition and the measurement light emitted from the light source and transmitted through the living body is detected by the plurality of sensors; and an analysis unit configured to analyze at least one of rectilinearity of the measurement light in the living body and an optical distance from the light source using a detection result of the measurement light detected by the detection unit.

According to the present disclosure, there is provided a measurement method including: emitting at least one kind of measurement light belonging to a predetermined wavelength band toward a measurement region formed by at least a part of a living body; detecting the measurement light emitted from a light source and transmitted through the living body by a plurality of sensors arranged regularly in a predetermined disposition; and analyzing at least one of rectilinearity of the measurement light in the living body and an optical distance from the light source using a detection result of the detected measurement light.

According to the present disclosure, there is provided a program causing a computer, capable of communicating with a measurement module including a light source that emits at least one kind of measurement light belonging to a predetermined wavelength band toward a measurement region formed by at least a part of a living body and a detection unit in which a plurality of sensors are arranged regularly in a predetermined disposition and the measurement light emitted from the light source and transmitted through the living body is detected by the plurality of sensors, to realize: an analysis function of analyzing rectilinearity of the measurement light in the living body and an optical distance from the light source using a detection result of the measurement light detected by the detection unit.

According to the present disclosure, there is provided a recording medium having the program recorded thereon.

According to the present disclosure, at least one kind of measurement light belonging to a predetermined wavelength band is emitted toward a measurement region formed by at least a part of a living body. The measurement light transmitted through the living body is detected by a detection unit in which a plurality of sensors are arranged regularly in a predetermined disposition. Rectilinearity of the measurement light in the living body and an optical distance from the light source are analyzed using a detection result of the detected measurement light.

Advantageous Effects of Invention

According to the present disclosure described above, it is possible to measure a form of light scattering in a body more simply.

Note that the effects described above are not necessarily limited, and along with or instead of the effects, any effect that is desired to be introduced in the present specification or other effects that can be expected from the present specification may be exhibited.

DESCRIPTION OF EMBODIMENTS

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

The description will be made in the following order.
1. Investigation by inventor
1.1 Human body skin structure model
1.2 Configuration of general measurement device
2. First Embodiment
2.1 Measurement device
2.2 Measurement method
2.3 Hardware configuration of measurement device

Investigation by Inventor

Figure 1:
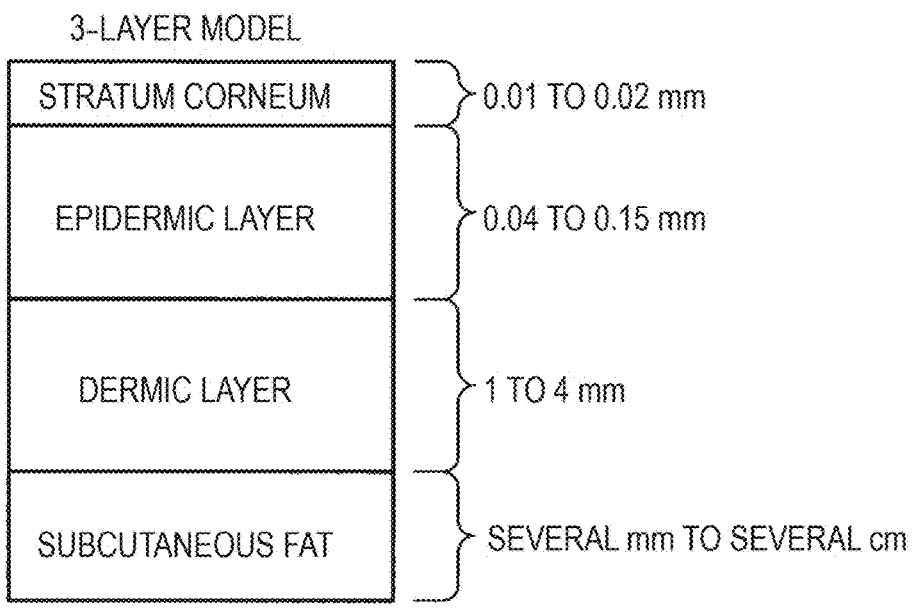
FIG. 1 is an explanatory diagram illustrating an exemplary human body's skin structure model.
Figure 2:
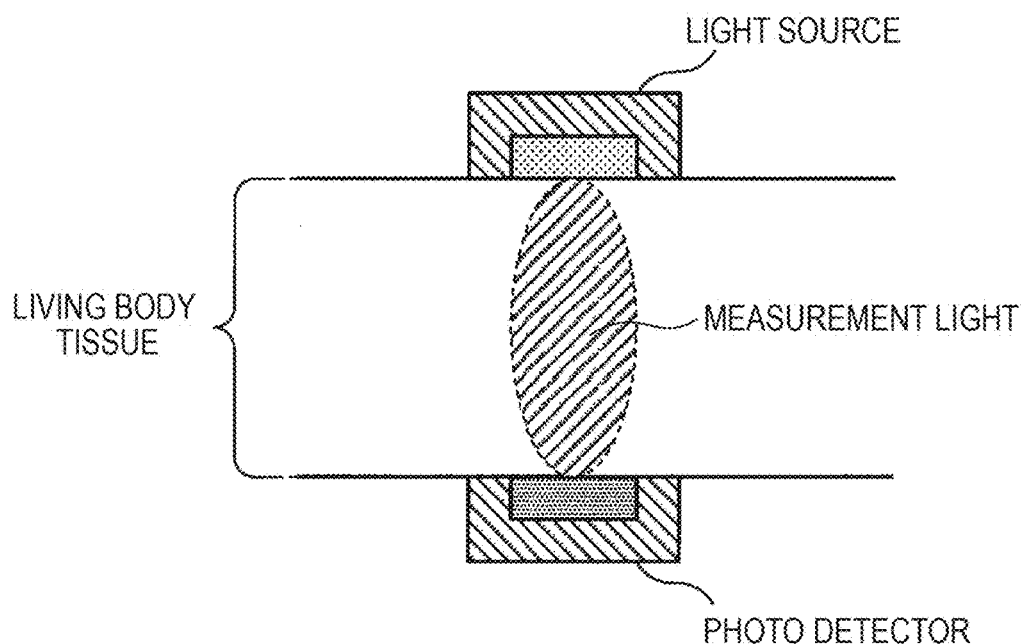
FIG. 2 is an explanatory diagram illustrating the configuration of a general measurement device.
Figure 3:
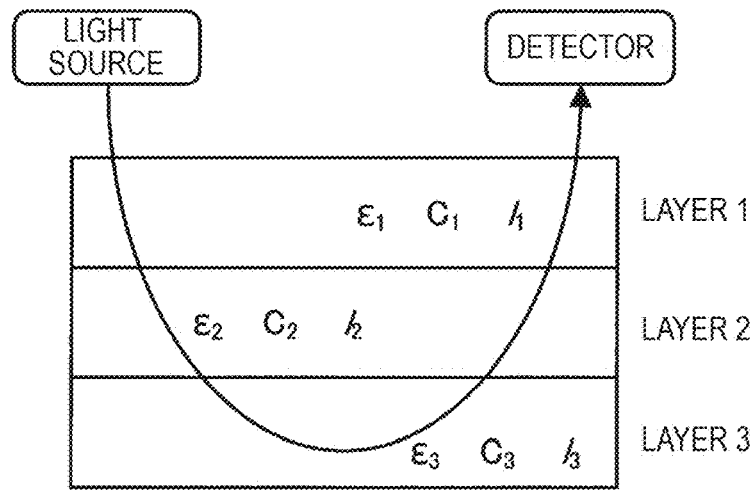
FIG. 3 is an explanatory diagram for explaining the extended Lambert-Beer law.

Content and results of investigation performed by the inventor will be first described with reference to FIGS. 1 to 4B before a measurement device and a measurement method according to an embodiment of the present disclosure are described. FIG. 1 is an explanatory diagram illustrating an exemplary human body skin structure model. FIG. 2 is an explanatory diagram for explaining the extended Lambert-Beer law. FIGS. 3 to 4B are explanatory diagrams illustrating the configuration of a general measurement device.
<Human Body Skin Structure Model>

First, a skin structure model obtained by modeling a human body skin structure will be described in brief with reference to FIG. 1.

As described above, there has been developed a technique for measuring blood and body fluid components such as glucose, albumin, AGEs (Advanced Glycation Endproducts), cholesterol, and oxygenated/reduction hemoglobin present in a human body with non-invasive optical measurement.

How a human body's skin structure is modeled is important for analyzing measured data. An exemplary human body's skin structure model is a 3-layer model as illustrated in FIG. 1.

The 3-layer model illustrated in FIG. 1 is such that subcutaneous tissues below the dermic layer and the stratum corneum of the skin are modelled into the three layers of epidermic layer, dermic layer and subcutaneous fat. In the 3-layer model, though depending on a person, the stratum corneum is equivalent to about 0.01 to 0.02 mm inward from the body surface, the epidermic layer is equivalent to about 0.04 to 0.15 mm from the body surface, the dermic layer is equivalent to about 1 to 4 mm from the body surface, and the subcutaneous fat is equivalent to about several millimeters to several centimeters from the body surface.

In the skin structure, melanin pigments are present in the epidermic layer, and capillaries are present in the dermic layer. Various blood components such as oxygenated hemoglobin and reduction hemoglobin are present in the capillaries, and fat cells are mainly present in the subcutaneous fat. Thus, a skin structure model to be taken into consideration is important for measuring the components with non-invasive optical measurement.

Incidentally, a human body that has the foregoing skin structure is a light-scattering body, and it is known that light with shorter wavelengths is scattered more easily. For example, a scattering coefficient of the skin of a human body with respect to light with a wavelength of 633 nm is 27 $mm^{-1}$ in the epidermic layer and the dermic layer and is 12.6 $mm^{-1}$ in the subcutaneous fat. On the other hand, in consideration of the skin structure model illustrated in FIG. 1, light is scattered mainly in the dermic layer and the subcutaneous fat. Light is rarely scattered in the epidermic layer.
<Configuration of General Measurement Device>

Next, a general configuration of a measurement device that measures blood and body fluid components (in-vivo components) such as glucose, albumin, advanced glycation end-products (AGEs), cholesterol, and oxygenated/reduction hemoglobin present in a human body with non-invasive optical measurement will be described in brief with reference to FIGS. 2 to 4B.

In the general measurement device, biological information is measured by a measurement unit to which a measurement probe is connected. As illustrated in FIG. 2, the measurement probe is configured to include a light source and a photo detector and measures a temporal change of light scattering by a living body. A measurement result regarding the light scattering measured by the measurement probe is output to an analysis unit, and the concentration or the like of an in-vivo component of interest is calculated based on the obtained measurement result.

In the measurement device, it is necessary to use light of at least one kind of wavelength as light (measurement light) to be emitted toward a living body. Here, as the measurement light, light with a wavelength belonging to a band from red light to near infrared light is often used since the light easily reaches the inside of a living body.

In the measurement probe of the measurement device, as illustrated in FIG. 2, the measurement light is emitted from the light source toward a skin surface of a living body to rectilinearly propagate, be reflected, or be diffused inside the living body, and thus exit light emitted from the living body is detected by the photo detector. Here, the transmissive measurement device illustrated in FIG. 2 is installed so that the light source and the photo detector face each other with a part of a living body (for example, a finger) interposed therebetween. The photo detector detects exit light transmitted while rectilinearly propagating or being diffused in the living body. At this time, the measurement light is partially absorbed by arteries, veins, or other body tissues in the living body and is measured as exit light.

The measurement device utilizes the extended Lambert-Beer law in order to associate measured actual data with the amount of photoabsorption due to an in-vivo component of interest (or oxygenated hemoglobin or reduction hemoglobin). The general measurement device takes into consideration propagation of light inside a living body in terms of a living body, or an object (light scattering body) for diffusing light, and thus the general Lambert-Beer law which does not take into consideration the scattering/diffusing effects cannot be used. Thus, the general measurement device utilizes the extended Lambert-Beer law indicated in the following Equation 11, thereby to analyze resultant measurement data. The extended Lambert-Beer law will be briefly described below with reference to FIG. 3.

[Math. 1]

$$A(\lambda) = -\log\frac{I(\lambda)}{I_0(\lambda)} = \sum_i A_i(\lambda) + G(\lambda) = \sum_i \varepsilon_i(\lambda)C_i l_i(\lambda) + G(\lambda) \quad \text{Equation 11}$$

where, in the above Equation 11, $\lambda$: Wavelength of light of interest, $A(\lambda)$: Degree of photoabsorption with wavelength $\lambda$, $I_0(\lambda)$: Intensity of light with wavelength $\lambda$ incident into scattering body, $I(\lambda)$: Detection intensity of light with wavelength $\lambda$ passing through scattering body, $G(\lambda)$: Amount of attenuation due to scattering of light with wavelength $\lambda$, and $\varepsilon_i(\lambda)$: Photoabsorption coefficient of light with wavelength $\lambda$ in substance i, which is specific to substance.

$C_i$: Concentration of substance i, and $I_i$: Average optical path length when light with wavelength $\lambda$ propagates in substance i.

There will be assumed herein that the extended Lambert-Beer law is applied to a scattering body having a layer structure as illustrated in FIG. 3. In the following, a subscript for specifying a layer is described as i and the number of substances contained in a layer i is indicated with a subscript j. The extended Lambert-Beer law for the scattering body having the layer structure as illustrated in FIG. 3 can be expressed in the following Equation 12 and Equation 13.

[Math. 2]

$$A(\lambda) = \quad \text{(Equation 12)}$$
$$-\log\frac{I(\lambda)}{I_0(\lambda)} = \sum_i A_i(\lambda) + G(\lambda) = \sum_i \varepsilon_i(\lambda)C_i l_i(\lambda) + G(\lambda)$$

$$A_i(\lambda) = \sum_j \varepsilon_{ij}(\lambda)C_{ij} l_i(\lambda) \quad \text{(Equation 13)}$$

where, in the Equation 12 and Equation 13, $\lambda$: Wavelength of light of interest, $A(\lambda)$: Degree of photoabsorption with wavelength $\lambda$, $I_0(\lambda)$: Intensity of light with wavelength $\lambda$ incident into scattering body, $I(\lambda)$: Detection intensity of light with wavelength $\lambda$ passing through scattering body, $G(\lambda)$: Amount of attenuation due to scattering of light with wavelength $\lambda$, $\varepsilon_i(\lambda)$: Photoabsorption coefficient of light with wavelength $\lambda$ in layer i, $C_i$: Concentration of substance contained in layer i, $I_i$: Average optical path length when light with wavelength $\lambda$ propagates in layer $\varepsilon_{ij}(\lambda)$: Photoabsorption coefficient of light with wavelength $\lambda$ in substance j contained in layer i, and $C_{ij}$: Concentration of substance j contained in layer i.

Herein, a photoabsorption coefficient of an in-vivo component of interest can be specified by previously measuring an absorption spectrum of the in-vivo component of interest or acquiring data from a well-known database. Thus, the photoabsorption coefficient of the in-vivo component of interest can be handled as the known amount by use of the data. The degree of photoabsorption in the leftmost side of Equation 12 can be calculated by measuring the detection intensity of the measurement light with each wavelength using the measurement device and comparing the measured detection intensity to the intensity of the measurement light before it enters the living body.

For hemoglobin in the blood of interest in the pulse oximeter, a degree of photoabsorption changes due to the presence of a bond with oxygen and the degree of photoabsorption is different depending on a wavelength to be observed. Therefore, the degrees of photoabsorption are measured at a plurality of wavelengths thereby to find a ratio between reduction hemoglobin (Hb) not bound with oxygen and oxygenated hemoglobin (HbO2).

A rate of oxygenated hemoglobin in the total hemoglobin contained in the blood is called blood oxygen saturation. Arterial oxygen saturation SaO2 is particularly helpful for biological information, and the oxygen saturation SaO2 can be calculated in the following Equation 14. SpO2 described above is percutaneously-measured SaO2.

[Math. 3]

$$\text{SaO}_2 = \frac{C_{HbO2}}{C_{HbO2} + C_{Hb}} \quad \text{Equation 14}$$

In the Equation 14,

SaO2: Arterial oxygen saturation, $C_{HbO2}$: Concentration of oxygenated hemoglobin, and $C_{Hb}$: Concentration of reduction hemoglobin.

As stated above, the exit light detected by the photo detector of the measurement probe in the measurement device is absorbed in the body tissues or blood components in a reflecting/scattering progress of the measurement light in the body. An intensity of the exit light is analyzed thereby to calculate SpO2, but SpO2 is arterial oxygen saturation, and thus an influence of photoabsorption due to any other than arterial blood is needed to be excluded from the exit light.

The elements causing photoabsorption of incident light can be largely classified into three types such as arterial blood, venous blood and other body tissues. At this time, the exit light is subjected to photoabsorption as indicated in the following Equation 15.

[Math. 4]

$$OD^\lambda = \log\left(\frac{I_0^\lambda}{I^\lambda}\right) =$$

$$\varepsilon_t^\lambda C_t d_t + \varepsilon_v^\lambda C_v d_v + (\varepsilon_{Hb}^\lambda C_{Hb} + \varepsilon_{HbO2}^\lambda C_{HbO2})d_a + B_S$$

Equation 15

In the Equation 15,
λ: Wavelength,
ε: Photoabsorption coefficient,
C: Concentration, and
d: Optical path length.

In the Equation 15, the first term in the rightmost side indicates photoabsorption caused by a component other than blood, the second term in the rightmost side indicates photoabsorption caused by venous blood, the third term in the rightmost side indicates photoabsorption caused by arterial blood, and the fourth term in the rightmost side indicates photoabsorption caused by diffusion in the living body.

The general measurement device uses the fact that pulsation is observed only in the arteries among the three elements, and may separate photoabsorption of the arterial blood from other elements. That is, the Equation 15 is temporally differentiated thereby to remove an influence of photoabsorption due to veins and other body tissues having no pulsation (or no temporal change). The differentiation operation corresponds to removal of a DC component by the frequency filter in a signal processing, and is none other than a pulse waveform extraction processing.

In the Equation 14, two unknown numbers for calculating SaO2 are the reduction hemoglobin concentration ($C_{Hb}$) and the oxygenated hemoglobin concentration ($C_{HbO2}$), and thus two measurement results need to be simultaneously obtained in order to specify the two unknown numbers. Thus, the measurement device uses at least two wavelengths to make measurements.

There will be assumed below a case in which measurements are made by two kinds of incident light with wavelengths λ1 and λ2 and temporal changes $\Delta OD^{\lambda 1}$ and $\Delta OD^{\lambda 2}$ of the intensities of the exit light are found. In this case, the temporal changes of the intensities of the exit light measured by the two wavelengths can be expressed in the following Equation 16 from the equation 15. Thus, the unknown hemoglobin concentration ($C_{Hb}$) and oxygenated hemoglobin concentration ($C_{HbO2}$) can be calculated as in the following Equation 17 by use of the photoabsorption coefficients of hemoglobin and oxygenated hemoglobin, and the measurement results.

[Math. 5]

$$\begin{bmatrix} \varepsilon_{Hb}^{\lambda 1} & \varepsilon_{HbO2}^{\lambda 1} \\ \varepsilon_{Hb}^{\lambda 2} & \varepsilon_{HbO2}^{\lambda 2} \end{bmatrix}\begin{bmatrix} C_{Hb} \\ C_{HbO2} \end{bmatrix} = \frac{1}{\Delta d_a}\begin{bmatrix} \Delta OD^{\lambda 1} \\ \Delta OD^{\lambda 2} \end{bmatrix}$$ (Equation 16)

$$\begin{bmatrix} C_{Hb} \\ C_{HbO2} \end{bmatrix} = \frac{1}{\Delta d_a}\begin{bmatrix} \varepsilon_{Hb}^{\lambda 1} & \varepsilon_{HbO2}^{\lambda 1} \\ \varepsilon_{Hb}^{\lambda 2} & \varepsilon_{HbO2}^{\lambda 2} \end{bmatrix}^{-1}\begin{bmatrix} \Delta OD^{\lambda 1} \\ \Delta OD^{\lambda 2} \end{bmatrix}$$ (Equation 17)

Therefore, when the Equation 17 is substituted into the Equation 14, the following Equation 18 is obtained. In the following Equation 18, the parameters α, β, and Φ are as in the following Equations 19a to 19c.

[Math. 6]

$$SaO_2 = \frac{C_{HbO2}}{C_{HbO2} + C_{Hb}}$$ (Equation 18)

$$= \frac{\varepsilon_{Hb}^{\lambda 1}\Delta OD^{\lambda 2} - \varepsilon_{Hb}^{\lambda 2}\Delta OD^{\lambda 1}}{\varepsilon_{HbO2}^{\lambda 1}\Delta OD^{\lambda 2} - \varepsilon_{HbO2}^{\lambda 2}\Delta OD^{\lambda 1}}$$

$$= \alpha + \beta \cdot \frac{\Delta OD^{\lambda 1}}{\Delta OD^{\lambda 2}}$$

$$= \alpha + \beta \cdot \Phi$$

$$\alpha = \frac{\varepsilon_{Hb}^{\lambda 1}}{\varepsilon_{Hb}^{\lambda 1} - \varepsilon_{HbO2}^{\lambda 1}}$$ (Equation 19a)

$$\beta = \frac{-\varepsilon_{HbO2}^{\lambda 2}}{\varepsilon_{Hb}^{\lambda 1} - \varepsilon_{HbO2}^{\lambda 1}}$$ (Equation 19b)

$$\Phi = \frac{\Delta OD^{\lambda 1}}{\Delta OD^{\lambda 2}}$$ (Equation 19c)

As is clear from the rightmost side in the Equation 18, it can be seen that the value of SaO2 is given as a function proportional to the parameter ΦD. The parameter Φ is a ratio between the amplitudes of the pulse waveforms measured at the waveform λ1 and the waveform λ2 as in the Equation 19c. The parameters α and β can be theoretically calculated from the photoabsorption coefficients of hemoglobin as illustrated in the Equation 19a and the Equation 19b, but in many cases, are required to be calibrated based on the transformation table obtained by previous experiments. This is because by doing so, a divergence between the condition under which the Lambert-Beer law is established and the actual condition in the living body can be corrected.

In accordance with such a method, the measurement device can also realize a function of a pulse oximeter by calculating arterial oxygen saturation SpO2 using the measurement result by two kinds of wavelengths.

By using the fact that diffusion coefficients are different in the layers (the epidermic layer, the dermic layer, and the subcutaneous fat) of the skin structure model illustrated in FIG. 1 or the fact that an in-vivo component or the like to be measured singularly absorbs light with a specific wavelength (that is, has absorption characteristics of a specific wavelength), the measurement device can calculate a component amount of an in-vivo component based on information (for example, a calibration curve) indicating a correlation between the scattering coefficient and the component amount of an in-vivo component of interest in regard to each type of measurement light used for measurement.

Figure 4A:
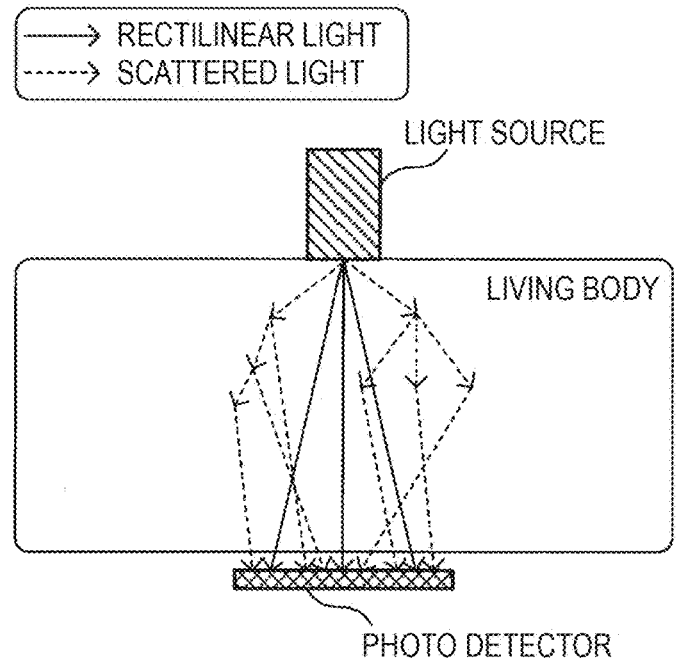
FIG. 4A is an explanatory diagram illustrating the configuration of a general measurement device.
Figure 4B:
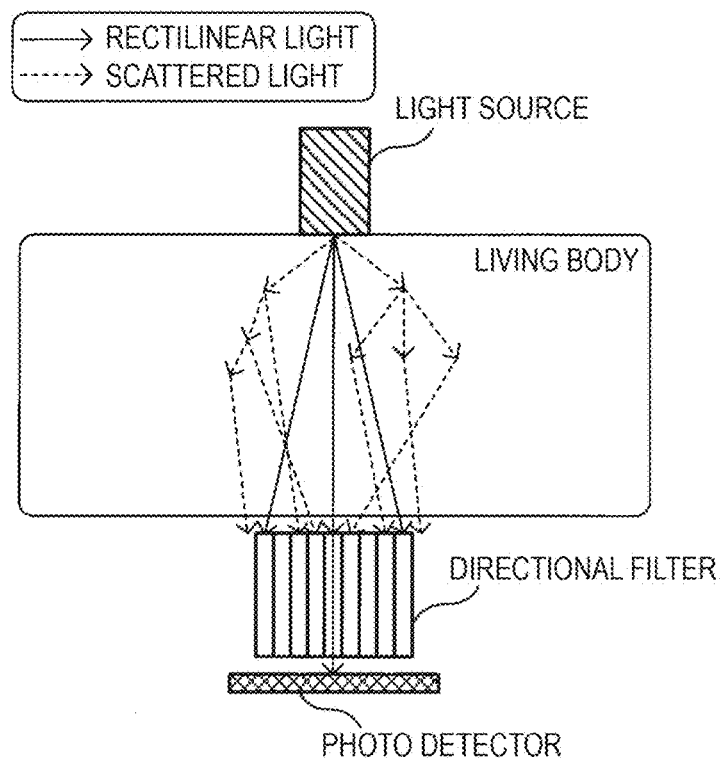
FIG. 4B is an explanatory diagram illustrating the configuration of a general measurement device.

Here, in a general measurement device, as illustrated in FIG. 4A, rectilinear light and scattered light are mixed to some extent in measurement light emitted from a light source such as a laser or an LED. Since rectilinear light and scattered light are mixed, the rectilinear light and the scattered light are imaged in the mixed state in a photo detector.

The scattered light passes further than the rectilinear light in a living body. Therefore, when a detection result in which the influence of the scattered light is superimposed is used, the scattered light is affected more than the rectilinear light due to in-vivo components. Accordingly, when analysis is performed using such a detection result, errors are superimposed on the detection result.

As a method of improving the influence of the scattered light, as illustrated in FIG. 4B, there is a method of using a directivity filter such as an optical fiber on the front stage of a photo detector. When the directivity filter is used, only light rectilinearly propagating in the living body (that is, rectilinear light) passes through the directivity filter and is imaged in the photo detector. However, a separation property of the scattered light becomes better when the directivity filter is used. However, since only light immediately below a light axis can be detected, sensitivity (a light-reception amount) may deteriorate. When the directivity filter is used, a light-reception amount considerably varies due to a slight deviation in the light axis caused by vibration of a body or a device, and thus practicality of use is low.

Accordingly, the inventor has thoroughly studied a measurement device capable of easily measuring a form of light scattering in a body, and thus has finalized a measurement device according to embodiments of the present disclosure to be described below.

First Embodiment

Figure 5:
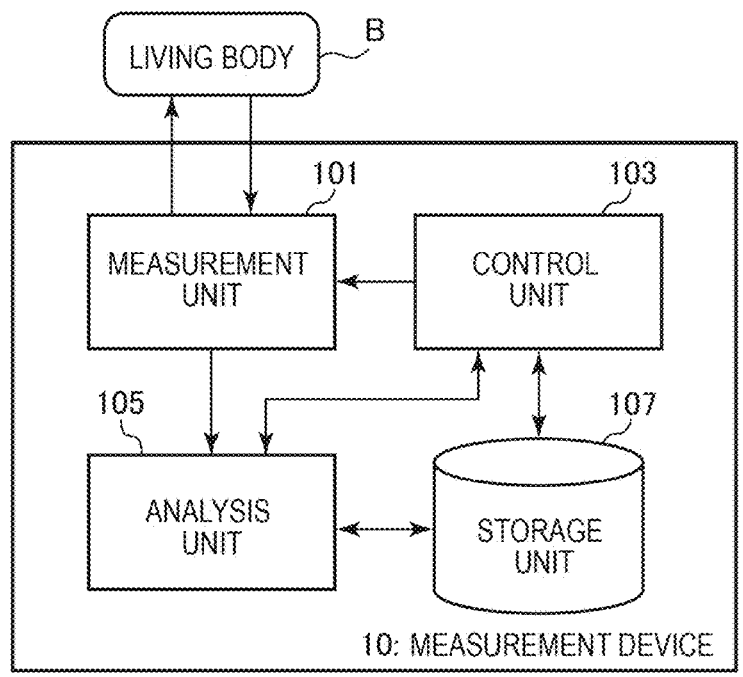
FIG. 5 is a block diagram illustrating a configuration of a measurement device according to a first embodiment of the present disclosure.
Figure 6:
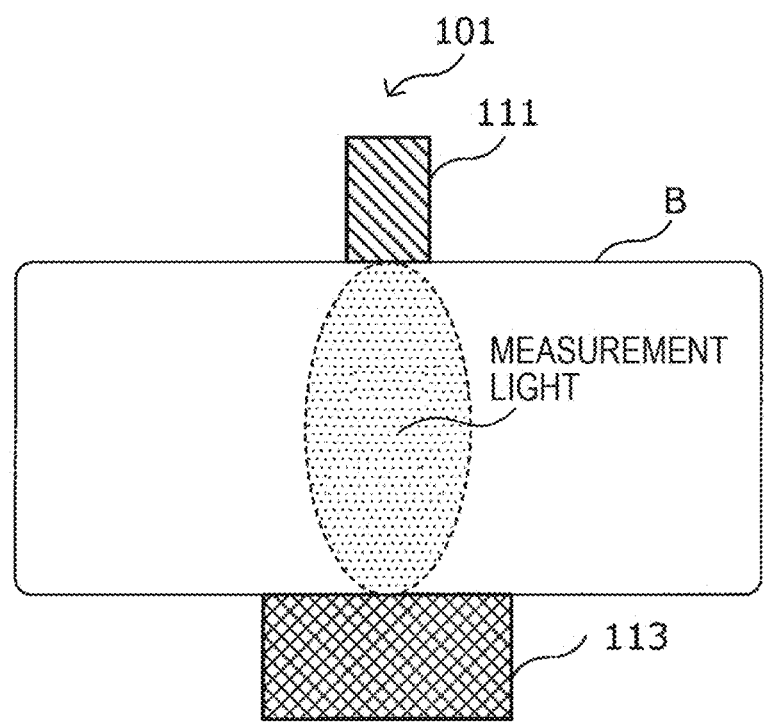
FIG. 6 is an explanatory diagram schematically illustrating an example of the configuration of a measurement unit included in the measurement device according to the embodiment.
Figure 7:
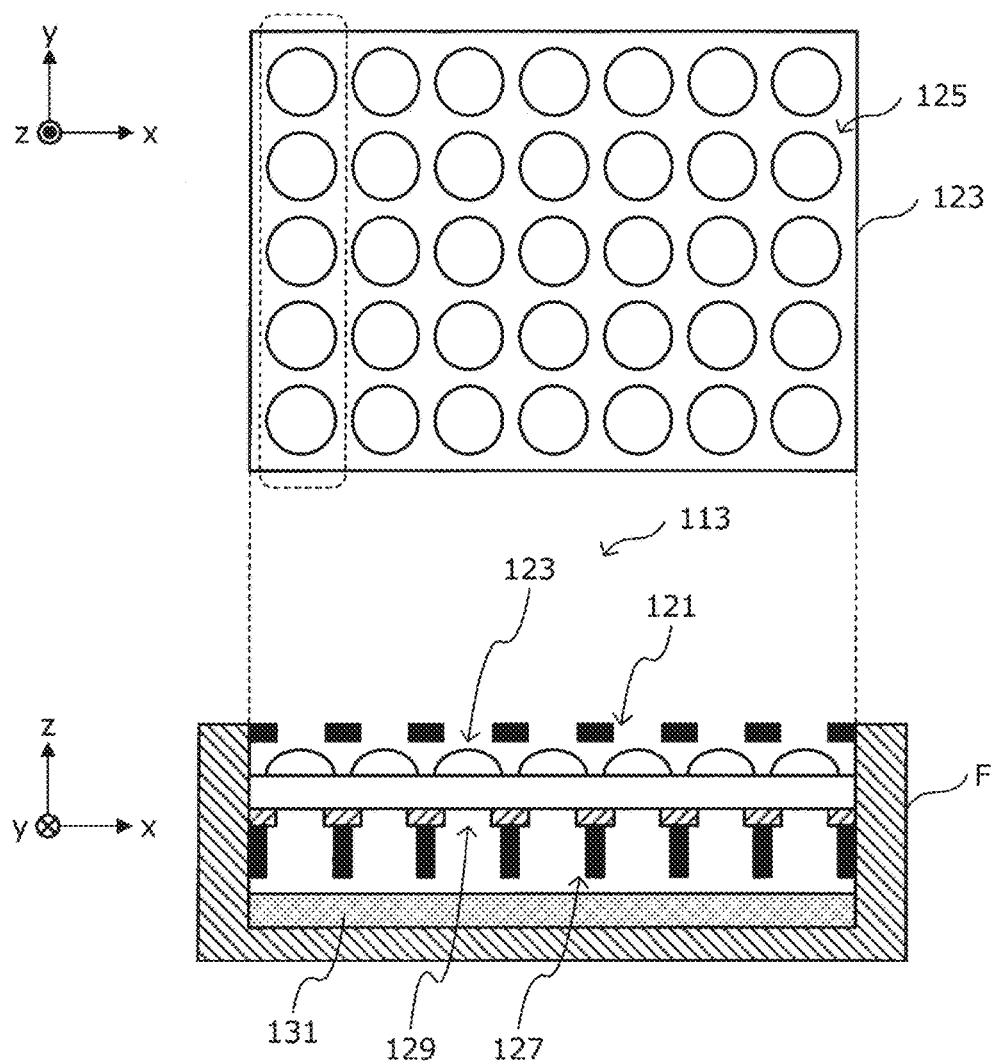
FIG. 7 is an explanatory diagram schematically illustrating the configuration of a detection unit included in the measurement unit according to the embodiment.
Figure 8:
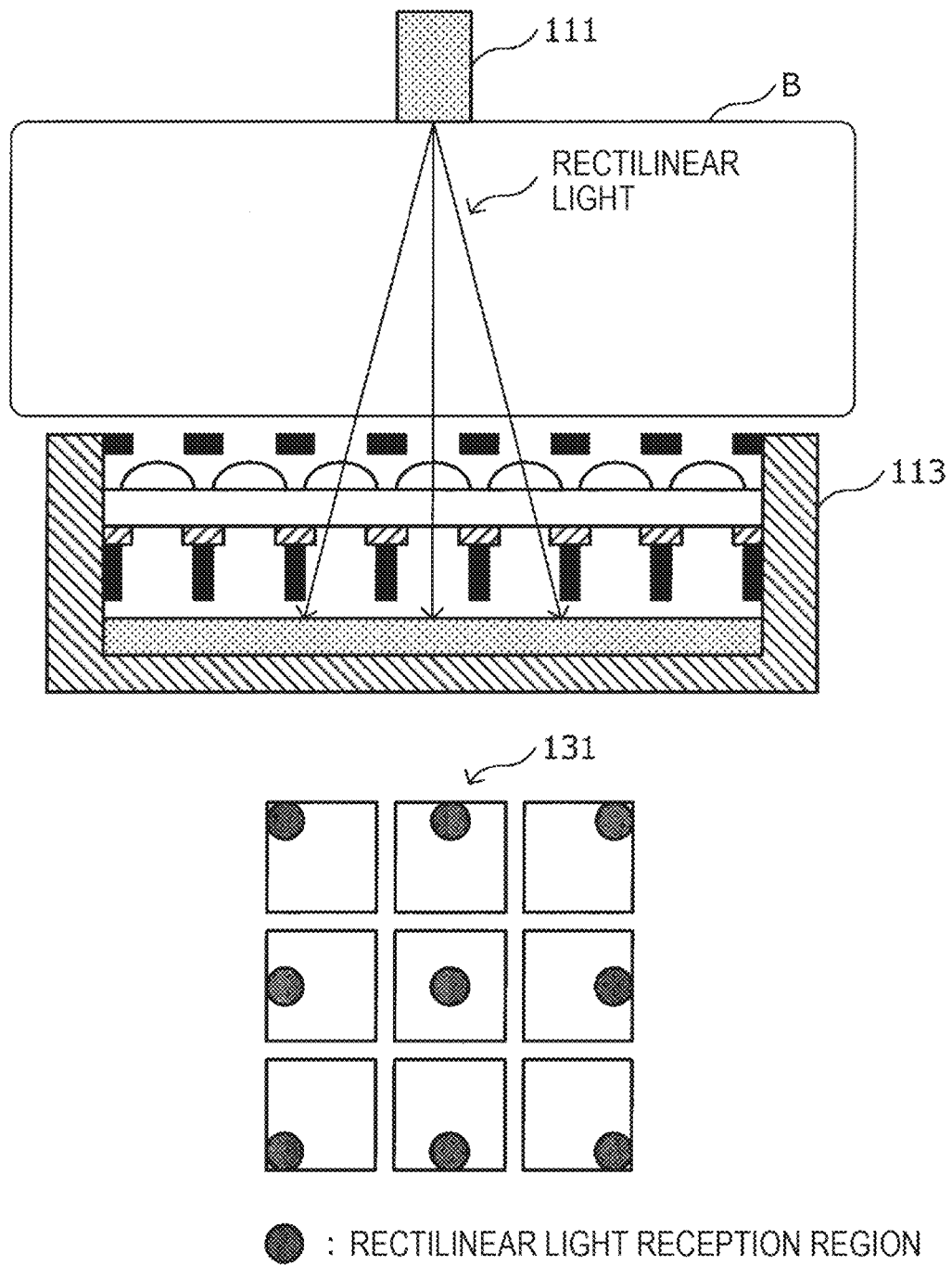
FIG. 8 is an explanatory diagram schematically illustrating a function of the detection unit included in the measurement unit according to the embodiment.
Figure 9:
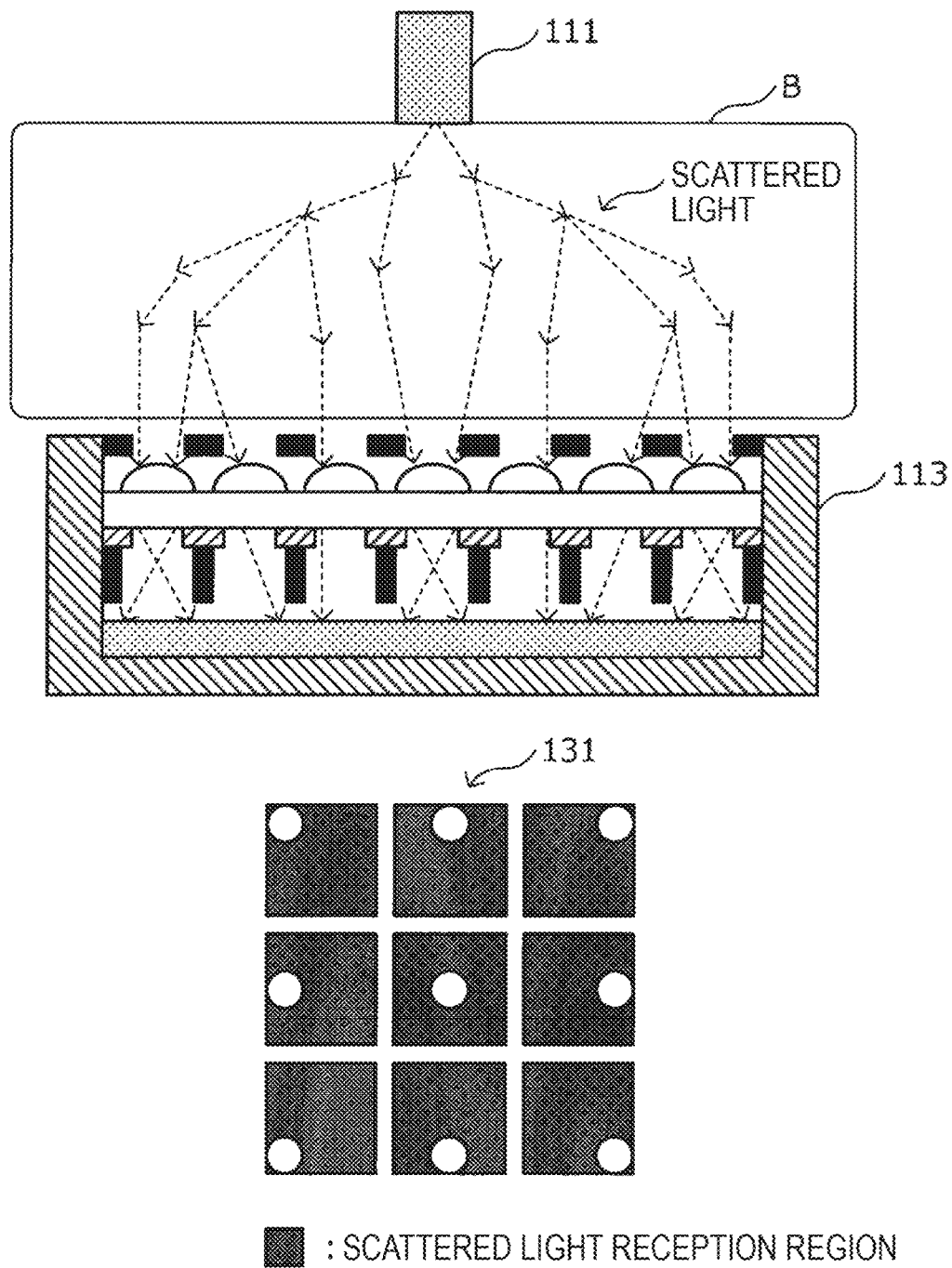
FIG. 9 is an explanatory diagram schematically illustrating a function of the detection unit included in the measurement unit according to the embodiment.

Hereinafter, a measurement device according to a first embodiment of the present disclosure will be described in detail with reference to FIGS. 5 to 9. FIG. 5 is a block diagram illustrating a configuration of a measurement device according to the present embodiment. FIG. 6 is an explanatory diagram schematically illustrating an example of the configuration of a measurement unit included in the measurement device according to the present embodiment. FIG. 7 is an explanatory diagram schematically illustrating the configuration of a detection unit included in the measurement unit according to the present embodiment. FIGS. 8 and 9 are explanatory diagrams schematically illustrating functions of the detection unit included in the measurement unit according to the present embodiment.

<Measurement Device>
[Overall Configuration of Measurement Device]

First, an overall configuration of a measurement device 10 according to the present embodiment will be described in detail with reference to FIG. 5.

The measurement device 10 according to the present embodiment is a device that measures a living body B which is a measurement target using light (measurement light) with a predetermined wavelength and analyzes rectilinearity of the measurement light inside the living body B and an optical distance from a light source based on the obtained measurement result. Based on the obtained measurement result, the measurement device 10 calculates component amounts of blood and body fluid components (in-vivo components) such as glucose, albumin, advanced glycation end-products (AGEs), cholesterol, oxygenated/reduction hemoglobin, and water, for example.

The measurement device 10 mainly includes a measurement unit 101 for measuring the living body B, a control unit 103, an analysis unit 105 and a storage unit 107 as illustrated in FIG. 5.

[Measurement Unit 101]

At first, a configuration of the measurement unit 101 according to the present embodiment will be specifically described with reference to FIG. 6 to FIG. 9. The measurement unit 101 according to the present embodiment is configured of a light source 111 and a detection unit 113 as illustrated in FIG. 6.

Light Source

The light source 111 is used to analyze rectilinearity of the measurement light in a living body and an optical distance from the light source and measure in-vivo components in the living body, and emits the measurement light belonging to a predetermined wavelength band toward the living body B. The light source 111 is arranged in a predetermined frame (not illustrated) so that an emission surface of the measurement light faces the living body B. The light source 111 emits light with a wavelength appropriate for measuring in-vivo components of interest with the measurement device 10 according to the present embodiment and can emit one type of light or a plurality of types of light.

The wavelength of the measurement light emitted by the light source 111 can be selected from wavelengths belonging to the visible light band to the near infrared band and can be appropriately set according to in-vivo components of interest. For example, when the light source 111 emits light with a wavelength of 940 nm or 950 nm, it is possible to obtain information about fat in a subcutaneous tissue. When the light source 111 emits light with a wavelength of 568 nm, 580 nm, 660 nm, or 890 nm, it is possible to obtain information about melanin pigments or blood components such as oxygenated hemoglobin and reduction hemoglobin. When the light source 111 emits light with a wavelength of 1400 nm to 2200 nm, it is possible to obtain information about glucose. For example, the light with the plurality of wavelengths may be emitted in a time-division manner from the light source 111, or the light with the plurality of wavelengths may also be simultaneously emitted and separated afterwards in the detection unit 113 to be described below by appropriately arranging optical filters with band restrictions.

Various wavelengths described above are merely exemplary, and the light emitted from the light source 111 in the measurement device 10 according to the present embodiment is not limited to the above examples.

The light source 111 may use a light emitting diode (LED), a small-sized laser, or the like, for example, and one or a plurality of such light emitting devices are provided for the light source 111.

The light source 111 is controlled by the control unit 103 described later in terms of an emission timing of the measurement light, an intensity of measurement light to be emitted, and the like.

The shape of the frame in which the light source 111 is arranged is not particularly limited.

Detection Unit

The detection unit 113 provided in the measurement device 10 according to the present embodiment has a plurality of sensors regularly arranged in a predetermined arrangement therein, and is directed for detecting measurement light emitted from the light source 111 and passing through the living body B with the sensors. In other words, the detection unit 113 according to the present embodiment is configured of a so-called multi-tap sensor. FIG. 7 illustrates a sensor utilizing a micro lens array (MLA) as an exemplary detection unit 113.

The detection unit 113 included in the measurement device 10 according to the present embodiment mainly includes, for example, a first light shield 121, a micro lens array 123, a second light shield 127, an aperture (diaphragm) 129, and a sensor 131, as illustrated in FIG. 7. In the detection unit 113, a transparent substrate through which light with a wavelength band to which the measurement light emitted from the light source 111 belongs can be transmitted may be provided at the previous stage of the first light shield 121. By providing the transparent substrate, it is possible to protect the detection unit 113 from a part of the living body B. Such a member is integrally held by a predetermined frame F.

The first light shield 121 functions as a directivity control plate for controlling directivity of measurement light passing through the living body B, and is provided at a boundary between mutually adjacent micro lenses 125 in the micro lens array 123 described later. The first light shield 121 is provided so that directivity of measurement light incident into each micro lens 125 can be controlled, which enables more precise measurement. The measurement light passing through the first light shield 121 is guided to the micro lens array 123.

The micro lens array 123 is configured of a plurality of micro lenses 125 as light receiving lenses as illustrated in the upper part of FIG. 7, and each micro lens 125 is arranged in the x direction and in the y direction on a predetermined substrate in a grid shape. Each micro lens 125 guides measurement light incident into the micro lens 125 to the sensor 131 described later. The micro lens array 123 has less curvature of field and has no distortion in the depth direction. Such a micro lens array 123 is used thereby to acquire favorable measurement data. Even if the living body B is present within the close-up distance, a depth of field of each micro lens 125 configuring the micro lens array 123 is set to cover the skin structure of interest (to focus up to a depth of several millimeters to several tens of millimeters from the body surface, for example) by the measurement device 10 according to the present embodiment.

The number of micro lenses 125 arranged in the micro lens array 123 according to the present embodiment is not limited to the example illustrated in the upper part of FIG. 7. The number of micro lenses 125 arranged in the micro lens array 123 according to the present embodiment can be freely set depending on a size of a living body to be shot or a size of the sensor 131.

Measurement light incident into the micro lens array 123 is focused into the micro lenses 125 to be image-formed to the sensor 131 described later.

Herein, the second light shield 127 and the aperture (diaphragm) 129 are provided at a boundary between mutually adjacent micro lenses 125 at the face of the micro lens array 123 on the sensor 131 side. The second light shield 127 and the aperture 129 enable directivity of measurement light passing through the micro lens array 123 to be controlled, and enables light incident into each micro lens 125 to be separated from light incident into an adjacent micro lens 125. Thereby, the measurement device 10 according to the present embodiment can select measurement light focused into the sensor 131.

The measurement device 10 according to the present embodiment is provided with various light shields or aperture as described above so that an incidence angle of light incident into each micro lens 125 is restricted, thereby preventing crosstalk between the micro lenses 125 caused by body scattering. Crosstalk between the micro lenses 125 is prevented thereby to acquire a signal obtained from sensor pixels corresponding to some micro lenses 125 among the micro lenses 125 provided in the micro lens array 123 (or a signal corresponding to a local position in the measurement region), thereby enhancing a temporal resolution and a spatial resolution of data measured by the sensor 131 described below.

The sensor 131 detects an intensity of measurement light at each position in the xy plane illustrated in the upper part of FIG. 7. The sensor 131 converts an intensity of measurement light received by a photo detector (PD) or the like into an electric signal to be output to the analysis unit 105 described later. The sensor 131 may employ a 2D area sensor such as photodiode, CCD (Charge Coupled Devices) image sensor, CMOS (Complementary Metal Oxide Semiconductor) image sensor, sensor using organic EL as light receiving device, or TFT (Thin Film Transistor) image sensor.

One or a plurality of pixels are arranged below one micro lens 125, and when a plurality of pixels are provided corresponding to one micro lens 125, the control unit 103 or software described later controls such that an invalid pixel caused by a distance between the micro lens 125 and the subject is not present.

The sensor 131 is controlled by the control unit 103 described later in terms of scan timing and the like, and can output a detection intensity at any position in the upper part of FIG. 7 to the analysis unit 105, for example.

The configuration of the measurement unit 101 according to the present embodiment has been described above in detail with reference to FIG. 7.

When a measurement operation is performed in the above-described measurement unit 101 in a place where there is outside light, there is a possibility of an influence of the outside light being superimposed on a detection result. Accordingly, a higher gain than the outside light which is continuous light can be obtained using a detection result of the sensor 131 at a time at which the measurement light emitted from the light source 111 is driven in a pulse form with an increased light intensity and the measurement light is synchronized with a driven pulse of the light source 111.

By arranging an optical filter with different band restrictions for each pixel or all the pixels of the sensor 131, for example, it is also possible to select a detection result of a singular wavelength such as 660 nm, 800 nm, 890 nm, or 940 nm.

By driving the light source 111 in a pulse form, light detected in a time period other than an emission timing can be considered to have received an influence of the outside light. Accordingly, by sensing the light detected in a time period other than the emission timing, the analysis unit 105 to be described below can determine that a measurement result is invalid when a considerably large influence of the outside light is detected.

Further, when a living body is moving during a measurement operation, an influence is exerted on a blood flow and there is a possibility of the influence being superimposed on a measured value. Accordingly, by detecting a case in which an output value such as 660 nm or 890 nm at which absorption of hemoglobin in blood is high becomes an amplitude considerably larger than a pulse wave, the analysis unit 105 to be described below can determine that the measurement has failed.

Data to be Measured by Measurement Unit

Data (measurement data) to be measured by the measurement unit 101 according to the present embodiment will be described below in detail with reference to FIG. 8 and FIG. 9.

Since a human body is a medium in which light is considerably scattered, the measurement light emitted from the light source 111 and incident on the living body B travels while rectilinearly propagating or being diffused in the living body B, and thus is detected by the detection unit installed at a certain position.

At this time, the detection unit farther away from the light source 111 can detect measurement light deeply scattered and returned to the body surface. Energy with a specific wavelength of the measurement light is absorbed due to various in-vivo components present on the optical path and its intensity attenuates depending on a length of a distance (optical distance) in which the light travels.

In the measurement device 10 according to the present embodiment, characteristics of light scattering and attenuation at the position of each sensor can be modeled using outputs (measurement data) from sensors located at different x coordinates illustrated in FIG. 7 based on such characteristics of light.

The detection unit 113 according to the present embodiment separates the measurement light detected by the detection unit 113 into rectilinear light and scattered light in terms of positions at which light received by the micro lenses 125 is selectively condensed by the apertures 129 or the like, as illustrated in FIGS. 8 and 9. That is, the detection unit 113 analyzes the influences of scattering of the measurement light according to the intensity of the detected measurement light and a degree of distribution of the measurement light imaged in the plurality of sensors and separates the measurement light detected by the detection unit 113 into the rectilinear light and the scattered light.

Specifically, the detection unit 113 sets regions (rectilinear light reception regions) of the sensor 131 which correspond to positions at which the rectilinear light from the light source 111 is imaged, as illustrated in FIG. 8, and regions (scattered light reception regions) of the sensor 131 which are complementary sets of the rectilinear light reception regions and correspond to positions at which the scattered light scattered in the living body is imaged, as illustrated in FIG. 9. Moreover, according to positions at which the light is imaged in the pixels included in the sensor 131, the detection unit 113 classifies components of the light detected in the rectilinear light reception regions as rectilinear light components and classifies components of the light detected in the scattered light reception regions as scattered light components.

By adopting the separation method by the detection unit 113 using the above-described micro lens array 123, the rectilinear light can be selectively received even for the pixels not at a vertical position from the light source 111. Accordingly, selectivity of the detection sensitivity and the rectilinear light can be compatible.

By adopting the method of separation into the rectilinear light and the scattered light described above in the measurement device 10 according to the present embodiment, it is possible to analyze an optical distance from the light source 111 according to the pixels and the rectilinear light reception regions in which the rectilinear light is imaged.

Here, the position, the shape, and the size of the rectilinear light reception region are not limited to the case illustrated in FIG. 8. The shape and the size of the rectilinear light reception region and the position of the rectilinear light reception region may be appropriately set by preliminary verification.

By providing an allowable error range to some extent for the size of the rectilinear light reception region, more reliable measurement than in the measurement device illustrated in FIG. 4B can be realized even when the deviation in the light axis occurs due to vibration or the like.

By combining a separation method using polarization in the related art with the method of separation into the rectilinear light and the scattered light described above, it is possible to realize measurement with better separation characteristics.

[Control Unit 103]

Returning to FIG. 5, the control unit 103 provided in the measurement device 10 according to the present embodiment will be described.

The control unit 103 is realized by CPU (Central Processing Unit), ROM (Read Only Memory), RAM (Random Access Memory), or the like, for example. The control unit 103 controls to drive the light source 111, the sensor 131 and the like provided in the measurement unit 101, thereby governing the total measurement processing on the living body B in the measurement unit 101. More specifically, the control unit 103 controls the driving of the sensor such as scan timing of the sensor 131 or selection of the sensor 131 for acquiring information based on a predetermined synchronization signal or the like. Further, the control unit 103 controls the driving of the light source 111 for emission timing or intensity of measurement light.

When the control unit 103 performs the driving control described above, the light source 111 of the measurement unit 101 can emit the measurement light with a predetermined wavelength at an appropriate timing and the analysis unit 105 to be described below can acquire the measurement data at any position on the sensor 131.

Measurement data measured by the measurement unit 101 the driving of which is controlled by the control unit 103 is output to the analysis unit 105 described later, where the measurement data is analyzed.

Herein, when controlling the measurement unit 101, the control unit 103 can refer to various programs, parameters, databases and the like recorded in the storage unit 107 described later.

[Analysis Unit 105]

The analysis unit 105 included in the measurement device 10 according to the present embodiment is realized by, for example, a CPU, a ROM, a RAM and the like. The analysis unit 105 analyzes rectilinearity of the measurement light in a living body and an optical distance from the light source using a detection result of the measurement light detected by the measurement unit 101.

More specifically, when the analysis unit 105 uses a detection result of the light detected in the rectilinear light reception region or the light detected in the scattered light reception region, as illustrated in FIGS. 8 and 9, it is possible to obtain information about the rectilinearity of the measurement light in the living body. The analysis unit 105 analyzes the optical distance from the light source 111 according to the rectilinear light reception regions of the pixels in which the rectilinear light is imaged.

The analysis unit 105 can calculate a scattering amount in the living body B by comparing the intensity of the light incident on the living body B to the intensity of the rectilinear light separated by the foregoing method and can calculate the scattering coefficient from the length of the optical path length. The analysis unit 105 has information (for example, a calibration curve) indicating correlation of the component amount (component concentration) of each in-vivo component with respect to the scattering coefficient, and thus can calculate the component amount of the in-vivo component from the calculated scattering coefficient based on the information indicating the correlation.

Here, the detection unit 113 according to the present embodiment is a so-called multi-tap sensor in which the plurality of sensors are regularly arranged in a predetermined disposition, as illustrated in FIG. 7. One pixel or a plurality of pixels correspond to one micro lens. Since images in the micro lenses are reversed vertically and horizontally, the analysis unit 105 can obtain a two-dimensional map in which a positional relation is corrected and which indicates a continuous light amount change by performing a reversion process and then combining 2-dimensional maps (in other words, images regarding the intensity of the detected light) regarding the intensity of the light output by the detection unit 113.

When the plurality of pixels correspond to one micro lens, the analysis unit 105 can improve precision of data by combining data of the plurality of pixels corresponding to one micro lens. The analysis unit 105 may perform a process of acquiring only a representative value in units of micro lenses and complementing the value of each micro lens with curve approximation.

The analysis unit 105 can also acquire an attenuation curve of luminance by the micro lenses in advance and correct a luminance gradient by the micro lenses using the attenuation curve.

When the detection unit 113 illustrated in FIG. 7 is used, the size of a formed image is changed on a sensor surface from each micro lens according to a subcutaneous depth at which information is acquired. Accordingly, for example, when body fluid components are desired to be measured in the dermic layer, the analysis unit 105 can obtain continuous images at a spot of interest by deciding and recombining cut ranges of the images so that the images in which information regarding positions with a depth of about 1 mm from a body surface is acquired can be continuous.

Here, the analysis unit 105 according to the present embodiment can model a skin structure at the position of each sensor by performing, for example, a multivariable analysis process using the foregoing extended Lambert-Beer law for each wavelength based on actually measured data acquired from the sensor at each x coordinate position illustrated in FIG. 7. The analysis unit 105 can also obtain an attenuation curve of the light intensity by plotting a degree of absorption of light by the in-vivo component at the position of each sensor. The attenuation curve can be generated for each wavelength of the measurement light and a characteristic wavelength is selected as the wavelength of the measurement light in absorption of the in-vivo component of interest. Accordingly, the attenuation curve regarding light with a certain wavelength is an attenuation curve indicating the degree of absorption by a certain in-vivo component.

For example, by using two kinds of light, light with a wavelength of 660 nm and light with a wavelength of 890 nm, as the measurement light to emit the light toward the living body B in a time division manner and, for example, detecting the intensity of the light in the time division manner, the analysis unit 105 can calculate an amount of melanin contained in the living body. The analysis unit 105 can estimate attenuation of the light caused by melanin in the light with the wavelength of 660 nm or estimate the attenuation of light caused by melanin in the light with the wavelength of 890 nm by generating the attenuation curve of the two wavelengths. By using the light with the wavelength of 660 nm as the measurement light, it is also possible to calculate the thickness of the dermic layer. Further, by using the light with the wavelength of 940 nm as the measurement light, it is possible to obtain an attenuation curve regarding fat. The analysis unit 105 can also calculate the thickness of a fat layer using the attenuation curve.

The analysis unit 105 can separate a temporal variation in the components in arterial blood by separating an influence of the in-vivo components in the arterial blood from an influence of the in-vivo components in venous blood based on the same principle as the foregoing pulse oximeter. Accordingly, it is possible to more accurately analyze the components in which the temporal variation is small.

The analysis unit 105 can use the component amounts calculated in this way or the attenuation curve generated in this way to correct detection intensity of the light with each wavelength. By using the component amounts or the attenuation curve to correct the detection intensity of the light, it is possible to compensate for an influence of photoabsorption by the in-vivo components.

For example, the light received by the entire sensor 131 is transmitted through the arterial blood, the venous blood, and the subcutaneous tissues. The analysis unit 105 can separate or remove arterial components by processing the same calculation as the foregoing pulse oximeter function in units of pixels.

When there are veins or arteries in a measured part, optical characteristics in blood are considerably different and there is a high possibility of an error occurring in an analysis result. Therefore, it is desirable to perform removal of singular points. Accordingly, the analysis unit 105 according to the present embodiment can perform handling by using an entire image which can be obtained by the multi-tap sensor illustrated in FIG. 7. That is, in a portion in which there are such blood vessels, measurement results are considered to transit discontinuously between sensors. Therefore, the analysis unit 105 can detect the foregoing portion as a singular point to correct or delete the portion in terms of discontinuity of such measured data. Similarly, the analysis unit 105 can also correct or delete a singular point such as a body hair, a birthmark, or a mole of a surface.

The analysis unit 105 can estimate a spot in which there are veins or arteries in terms of an increase in the amount of oxygen in the veins or arteries using estimated images by two wavelengths of 660 nm and 890 nm and can estimate positions at which the veins and the arteries are located by specifying a spot in which a temporal change is large due to pulsation through dynamic image processing.

Further, the analysis unit 105 can also estimate the scattering coefficient in each spot by extracting the components of only veins or arteries.

The analysis unit 105 according to the present embodiment has been described in detail above.

[Storage Unit 107]

Returning to FIG. 5, the storage unit 107 provided in the measurement device 10 according to the present embodiment will be described.

The storage unit 107 is realized by the RAM, a storage device, or the like provided in the measurement device 10 according to the present embodiment. The storage unit 107 stores therein data on photoabsorption spectra or light scattering spectra used for the analysis processing in the analysis unit 105, a look-up table of various databases, and the like. The storage unit 107 may store therein measurement data measured by the measurement unit 101 according to the present embodiment, various programs or parameters or items of data used for the processing performed by the control unit 103 or the analysis unit 105 according to the present embodiment, and the like. The storage unit 107 can store, in addition to the above data, various parameters, processing progresses, and the like which need to be stored for any processing of the measurement device 10, as needed. Each processing unit such as the measurement unit 101, the control unit 103 or the analysis unit 105 can freely access the storage unit 107 and can write or read data in or from the storage unit 107.

The configuration of the measurement device 10 according to the present embodiment has been described above in detail with reference to FIG. 5 to FIG. 9.

The measurement device 10 according to the above-described embodiment can accurately estimate the in-vivo components leading to a variation in an optical model (skin structure model).

The control unit 103 and the analysis unit 105 according to the present embodiment may be part of the measurement device 10 according to the present embodiment, or may be realized by an external device such as computer connected to the measurement device 10. Measurement data generated by the measurement unit 101 is stored in a removable storage medium and the storage medium is removed from the measurement device 10 to be connected to other device having the analysis unit 105, and thus the measurement data may be analyzed.

Heretofore, an example of the functions of the measurement device 10 according to the present embodiment has been shown. Each of the above-described structural elements of other than the measurement unit 101 may be configured using a general-purpose material or a general-purpose circuit, or may be configured from hardware dedicated to the function of each structural element. Also, a CPU or the like may perform all the functions of the structural elements. Accordingly, the configuration to be used can be changed as appropriate according to the technical level at the time of carrying out the present embodiment.

A computer program realizing functions of the control unit and the analysis unit according to the above-described embodiment or a computer program controlling the control unit and the analysis unit according to the above-described embodiment can be generated and mounted on a personal computer or the like. A recording medium in which such computer program is stored and which can be read by a computer can also be provided. The recording medium is a magnetic disk, an optical disk, a magneto-optical disk, a flash memory, or the like, for example. Also, the computer program may be distributed via a network, for example, without using a recording medium.

[Modification Example of Measurement Unit 101]

Figure 10:
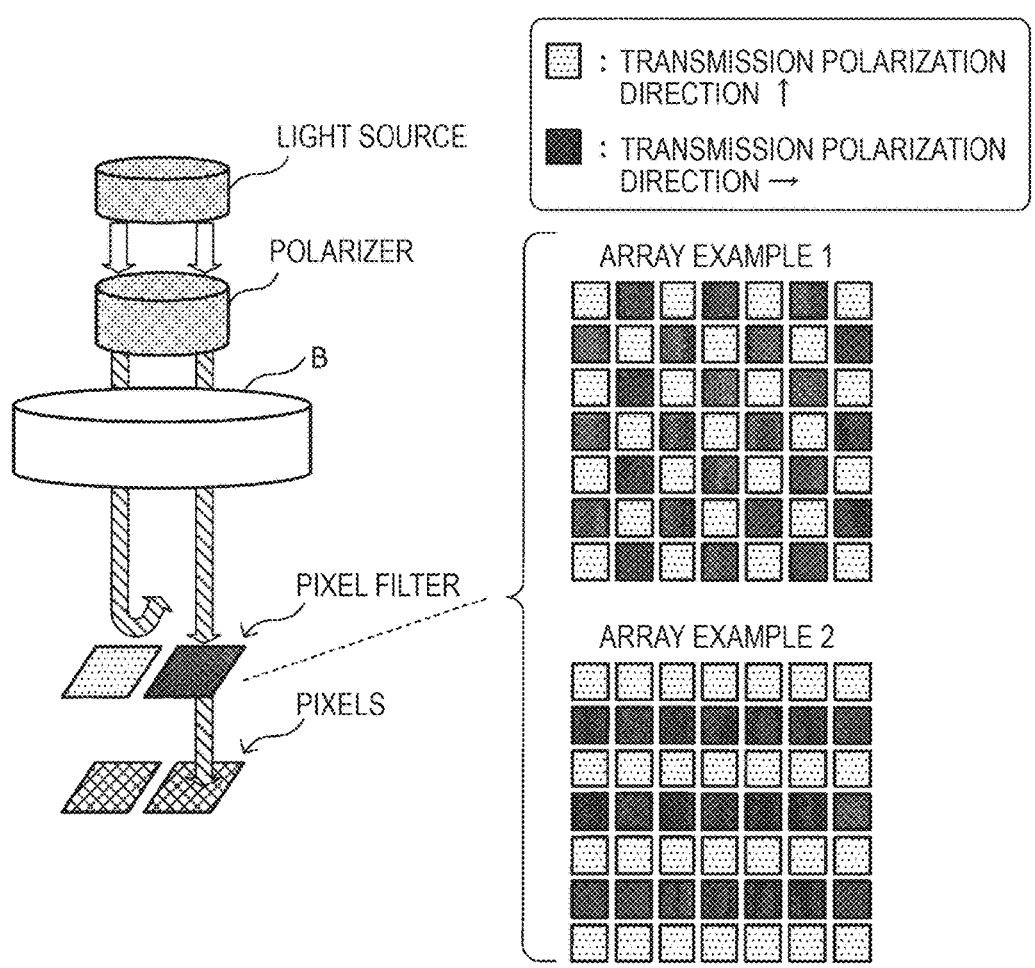
FIG. 10 is an explanatory diagram schematically illustrating another example of the configuration of the measurement unit included in the measurement device according to the embodiment.

Next, a modification example of the measurement unit 101 according to the present embodiment will be described in brief with reference to FIG. 10. FIG. 10 is an explanatory diagram schematically illustrating another example of the configuration of the measurement unit 101 included in the measurement device 10 according to the present embodiment.

There is an image sensor in which the direction of a polarizer is orthogonal (or has a difference of a given angle) in units of pixels, units of lines, or the like. In the image sensor, for example, as illustrated in FIG. 10, a pixel filter that selects a polarization direction is provided as a polarizer at the previous stage of the pixels of the sensor. Accordingly, by using the pixel polarization image sensor, the same advantageous effect as in phase modulation by liquid crystal of the related art can be realized on the side of the sensor.

In the case of this scheme, as illustrated in FIG. 10, rectilinear light and scattered light can be separated merely by arranging a fixed polarizer on the side of the light source.

By combining the pixel polarization image sensor with the multi-tap sensor illustrated in FIG. 7, a ratio between the rectilinear light and the scattered light for which the degree of separation is higher can be obtained with both pixel positions and polarized light. That is, when there is no living body, polarized light passing through the polarizer is received only in the pixels of the same direction and is not received in the orthogonal pixels. However, when there is a living body, light is considerably scattered in the living body. Therefore, a ratio between rectilinear light and scattered light changes depending on a change in a scattering coefficient. Specifically, as the scattering coefficient in a body is smaller, a light-reception amount of the transmission pixels increases and a light-reception amount of the non-transmission pixels decreases. Accordingly, using such information, it is possible to calculate a ratio between rectilinear light and scattered light with high precision.

As a technology for causing pixels to have polarization, for example, there is self-cloning photonic crystal.

The modification example of the measurement unit 101 according to the present embodiment has been described in brief above with reference to FIG. 10.

<Measurement Method>

Figure 11:
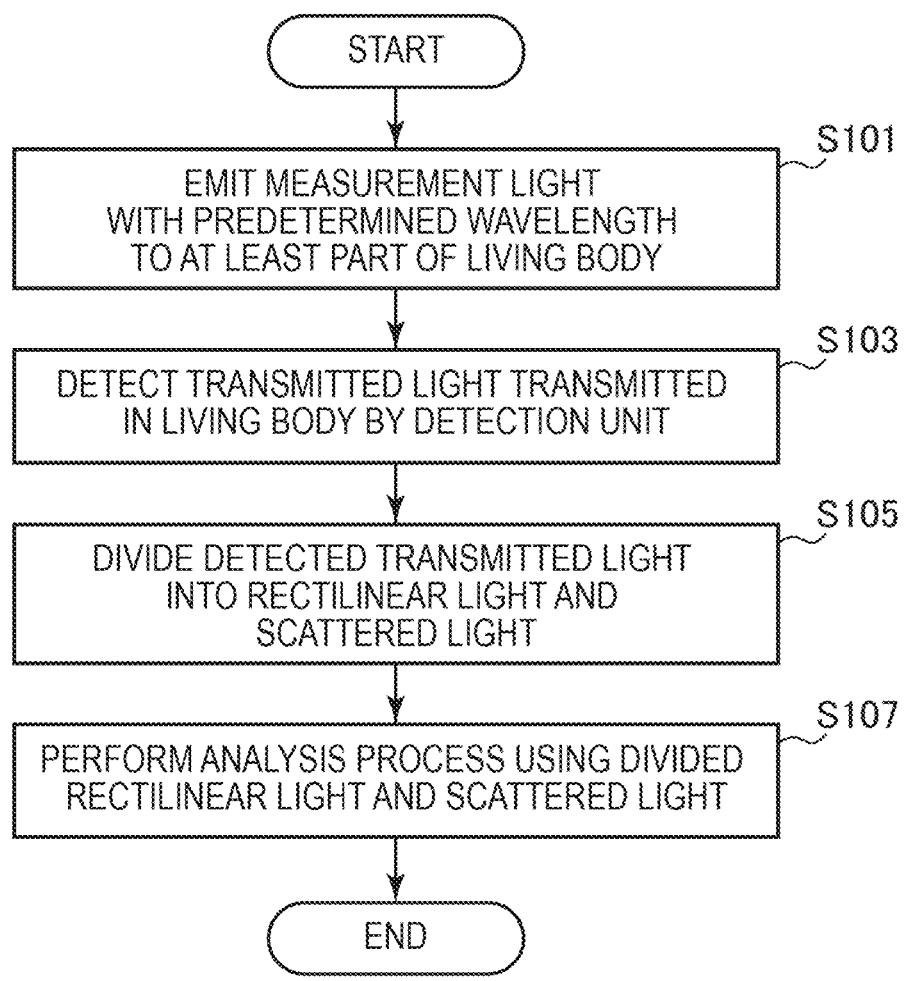
FIG. 11 is a flowchart illustrating an example of the flow of a measurement method according to the embodiment.

Next, the flow of a measurement method performed by the measurement device 10 according to the present embodiment will be described in brief with reference to FIG. 11. FIG. 11 is a flowchart illustrating an example of the flow of the measurement method according to the present embodiment.

In the measurement method according to the present embodiment, measurement light with a predetermined wavelength is first emitted toward at least a part of a living body from the light source 111 of the measurement unit 101 under the control of the control unit 103 (step S101). Thereafter, transmitted light transmitted rectilinearly or while being diffused in the living body is detected by the detection unit 113 of the measurement unit 101 (step S103). A detection result by the detection unit 113 is output to the analysis unit 105.

The analysis unit 105 divides the detected transmitted light into rectilinear light and scattered light in accordance with the method described above with reference to FIGS. 8 and 9 (step S105). Thereafter, the analysis unit 105 performs the foregoing various analysis processes using the divided rectilinear light and scattered light (step S107).

Accordingly, in the measurement method according to the present embodiment, it is possible to obtain various information about the component amount of the in-vivo component present in the living body as well as the information regarding the rectilinearity of the measurement light in the living body and the information regarding the optical distance from the light source.

The example of the flow of the measurement method according to the present embodiment has been described in brief above with reference to FIG. 11.

<Hardware Configuration>

Figure 12:
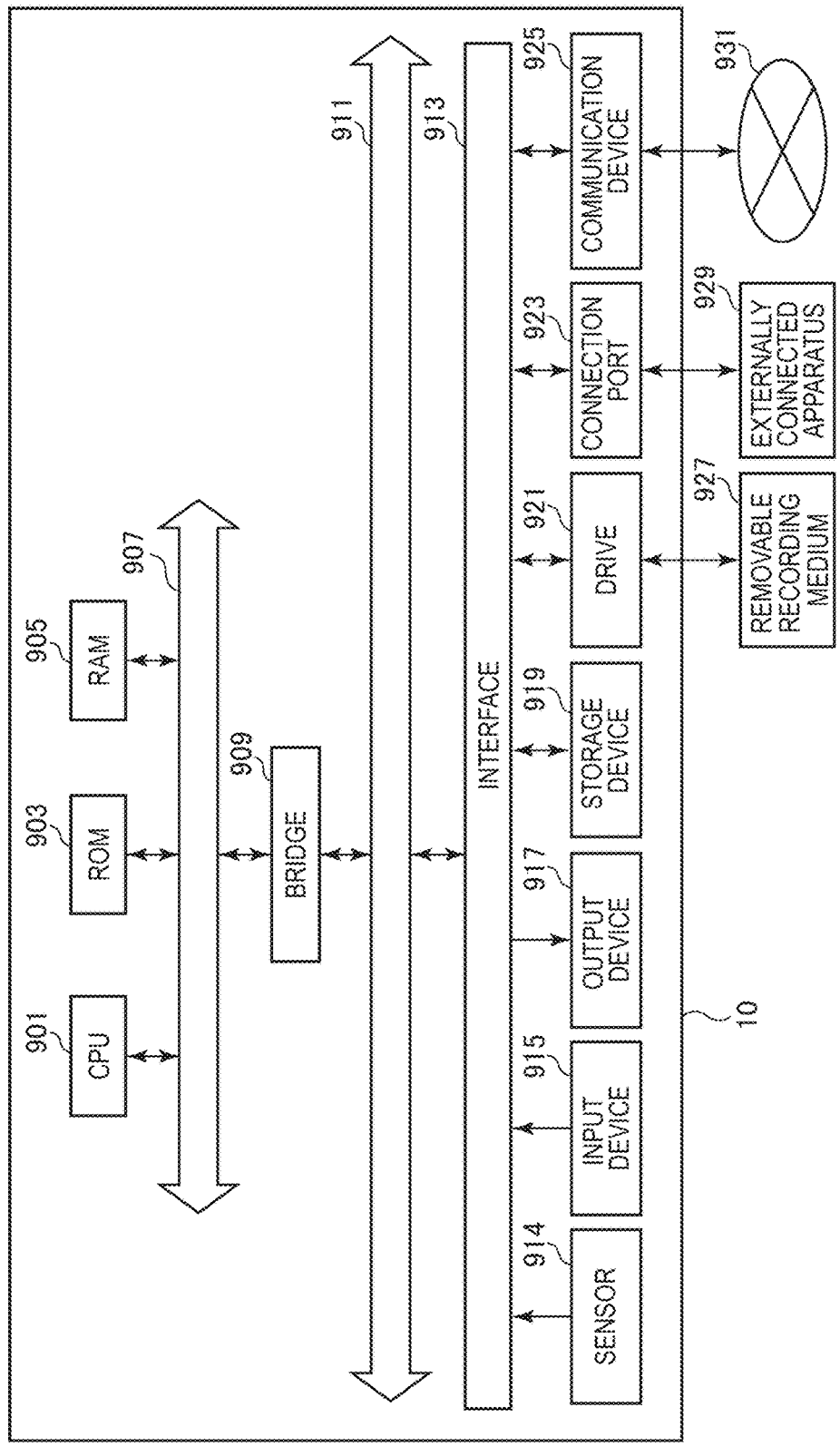
FIG. 12 is a block diagram for illustrating the hardware configuration of a measurement device according to an embodiment of the present disclosure.

Next, the hardware configuration of the measurement device 10 according to the embodiment of the present disclosure will be described in detail with reference to FIG. 12. FIG. 12 is a block diagram for illustrating the hardware configuration of the measurement device 10 according to the embodiment of the present disclosure.

The measurement device 10 mainly includes a CPU 901, a ROM 903, and a RAM 905. Furthermore, the measurement device 10 also includes a host bus 907, a bridge 909, an external bus 911, an interface 913, a sensor 914, an input device 915, an output device 917, a storage device 919, a drive 921, a connection port 923, and a communication device 925.

The CPU 901 serves as an arithmetic processing apparatus and a control device, and controls the overall operation or a part of the operation of the measurement device 10 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The sensor 914 is detecting means for detecting biological information unique to a user or various types of information to be used to acquire such biological information. This sensor 914 includes, for example, various imaging devices such as a CCD (Charge Coupled Device) or a CMOS (Complementary Metal Oxide Semiconductor) and the like. In addition, the sensor 914 may further have optics such as a lens to be used to image a spot of a living body or a light source and the like. The sensor 914 may also be a microphone and the like for acquiring sound and the like. Note that in addition to those mentioned above, the sensor 914 may also include various measuring instruments such as a thermometer, an illuminance meter, a hygrometer, a speedometer, an accelerometer, and the like.

The input device 915 is an operation means operated by a user, such as a mouse, a keyboard, a touch panel, buttons, a switch and a lever. Also, the input device 915 may be a remote control means (a so-called remote control) using, for example, infrared light or other radio waves, or may be an externally connected apparatus 929 such as a mobile phone or a PDA conforming to the operation of the measurement device 10. Furthermore, the input device 915 generates an input signal based on, for example, information which is input by a user with the above operation means, and is configured from an input control circuit for outputting the input signal to the CPU 901. The user of the measurement device 10 can input various data to the measurement device 10 and can instruct the measurement device 10 to perform processing by operating this input apparatus 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processing performed by the measurement device 10. More specifically, the display device displays, in the form of texts or images, a result obtained by various processes performed by the measurement device 10. On the other hand, the audio output device converts an audio signal such as reproduced audio data and sound data into an analog signal, and outputs the analog signal.

The storage device 919 is a device for storing data configured as an example of a storage unit of the measurement device 10 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside.

The drive 921 is a reader/writer for recording medium, and is embedded in the measurement device 10 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the measurement device 10. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected apparatus 929 connecting to this connection port 923, the measurement device 10 directly obtains various data from the externally connected apparatus 929 and provides various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the measurement device 10 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

A measurement device including:
a light source configured to emit at least one kind of measurement light belonging to a predetermined wavelength band toward a measurement region formed by at least a part of a living body;
a detection unit configured such that a plurality of sensors are arranged regularly in a predetermined disposition and the measurement light emitted from the light source and transmitted through the living body is detected by the plurality of sensors; and
an analysis unit configured to analyze rectilinearity of the measurement light in the living body and an optical distance from the light source using a detection result of the measurement light detected by the detection unit.

(2)

The measurement device according to (1),
wherein, in the detection unit, the measurement light transmitted through the living body is detected by a sensor using a micro lens array in which a plurality of lenses are regularly arranged in a grid shape.

(3)

The measurement device according to (1) or (2),
wherein detection precision of the measurement light is controlled in accordance with distribution density of the plurality of sensors in the detection unit, and
the analysis unit analyzes an influence of scattering of the measurement light by an in-vivo component contained in the living body according to intensity of the detected measurement light and a degree of distribution of the measurement light imaged in the plurality of sensors.

(4)

The measurement device according to any one of (1) to (3),
wherein the analysis unit divides the detected measurement light into rectilinear light rectilinearly propagating in the living body and scattered light transmitted through the living body while being scattered, and calculates a scattering coefficient corresponding to the in-vivo component based on a detection result corresponding to the rectilinear light.

(5)

The measurement device according to (4),
wherein the analysis unit divides the measurement light in the plurality of sensors into the rectilinear light and the scattered light according to imaging positions of the measurement light in the plurality of sensors.

(6)

The measurement device according to (4),
wherein a polarization direction of the measurement light is controlled to a predetermined direction before the measurement light is incident on the living body,
a polarization selection filter that selects one of two mutually orthogonal polarization directions as the polarization direction of the measurement light imaged in each of the plurality of sensors is provided at a previous stage of the plurality of sensors in the detection unit, and
the analysis unit divides the measurement light into the rectilinear light and the scattered light according to whether the measurement light is detected in the sensor corresponding to the polarization selection filter.

(7)

The measurement device according to any one of (4) to (6),
wherein the analysis unit calculates a component amount of the in-vivo component based on the calculated scattering coefficient.

(8)

The measurement device according to any one of (3) to (7),
wherein a wavelength of the measurement light emitted from the light source is controlled according to the in-vivo component of interest.

(9)

The measurement device according to any one of (3) to (8),
wherein the analysis unit performs an analysis process excluding the detection result corresponding to a spot of the living body causing an error in an analysis result of the in-vivo component.

(10)

The measurement device according to any one of (3) to (9),
wherein the in-vivo component is at least one of melanin, a blood component, and water.

(11)

A measurement method including:
emitting at least one kind of measurement light belonging to a predetermined wavelength band toward a measurement region formed by at least a part of a living body;
detecting the measurement light emitted from a light source and transmitted through the living body by a plurality of sensors arranged regularly in a predetermined disposition; and
analyzing rectilinearity of the measurement light in the living body and an optical distance from the light source using a detection result of the detected measurement light.

(12)

A program causing a computer, capable of communicating with a measurement module including a light source that emits at least one kind of measurement light belonging to a predetermined wavelength band toward a measurement region formed by at least a part of a living body and a detection unit in which a plurality of sensors are arranged regularly in a predetermined disposition and the measurement light emitted from the light source and transmitted through the living body is detected by the plurality of sensors, to realize:
an analysis function of analyzing rectilinearity of the measurement light in the living body and an optical distance from the light source using a detection result of the measurement light detected by the detection unit.

(13)

A recording medium having a program recorded thereon, the program causing a computer, capable of communicating with a measurement module including a light source that emits at least one kind of measurement light belonging to a predetermined wavelength band toward a measurement region formed by at least a part of a living body and a detection unit in which a plurality of sensors are arranged regularly in a predetermined disposition and the measurement light emitted from the light source and transmitted through the living body is detected by the plurality of sensors, to realize:
an analysis function of analyzing rectilinearity of the measurement light in the living body and an optical distance from the light source using a detection result of the measurement light detected by the detection unit.

REFERENCE SIGNS LIST 10 measurement device
101 measurement unit
103 control unit 105 analysis unit
107 storage unit
111 light source
121 first light shield
123 micro lens array
125 micro lens
127 second light shield
129 aperture (diaphragm)
131 sensor

The invention claimed is:

1. A measurement device comprising:
a light source configured to emit at least one kind of measurement light belonging to a predetermined wavelength band toward a measurement region formed by at least a part of a living body;
a detection unit configured such that a plurality of sensors are arranged regularly in a predetermined disposition and the measurement light emitted from the light source and transmitted through the living body is detected by the plurality of sensors, wherein each sensor of the plurality of sensors comprises a light reception region including a rectilinear light reception region that obtains a measurement of rectilinear light transmitted through the living body and a scattered light reception region that obtains a measurement of scattered light transmitted through the living body, the scattered light reception region being different from the rectilinear light reception region; and
a processor including processing circuitry and a memory device containing instructions that, when executed by the processing circuitry, are configured to analyze rectilinearity of the measurement light in the living body and an optical distance from the light source using a detection result of the measurement light detected by the detection unit.

2. The measurement device according to claim 1, wherein, in the detection unit, the measurement light transmitted through the living body is detected by the plurality of sensors using a micro lens array in which a plurality of lenses are regularly arranged in a grid shape.

3. The measurement device according to claim 2,
wherein detection precision of the measurement light is controlled in accordance with distribution density of the plurality of sensors in the detection unit, and
the instructions are configured to analyze an influence of scattering of the measurement light by an in-vivo component contained in the living body according to intensity of the detected measurement light and a degree of distribution of the measurement light imaged in the plurality of sensors.

4. The measurement device according to claim 3,
wherein the instructions are configured to divide the detected measurement light into rectilinear light rectilinearly propagating in the living body and scattered light transmitted through the living body while being scattered, and to calculate a scattering coefficient corresponding to the in-vivo component based on a detection result corresponding to the rectilinear light.

5. The measurement device according to claim 4,
wherein the instructions are configured to divide the measurement light in the plurality of sensors into the rectilinear light and the scattered light according to imaging positions of the measurement light in the plurality of sensors.

6. The measurement device according to claim 4,
wherein a polarization direction of the measurement light is controlled to a predetermined direction before the measurement light is incident on the living body,
a polarization selection filter that selects one of two mutually orthogonal polarization directions as the polarization direction of the measurement light imaged in each of the plurality of sensors is provided at a previous stage of the plurality of sensors in the detection unit, and
the instructions are configured to divide the measurement light into the rectilinear light and the scattered light according to whether the measurement light is detected in the sensor corresponding to the polarization selection filter.

7. The measurement device according to claim 4,
wherein the instructions are configured to calculate a component amount of the in-vivo component based on the calculated scattering coefficient.

8. The measurement device according to claim 3,
wherein a wavelength of the measurement light emitted from the light source is controlled according to the in-vivo component of interest.

9. The measurement device according to claim 3,
wherein the instructions are configured to perform an analysis process excluding the detection result corresponding to a spot of the living body causing an error in an analysis result of the in-vivo component.

10. The measurement device according to claim 3,
wherein the in-vivo component is at least one of melanin, a blood component, and water.

11. A measurement method comprising:
emitting at least one kind of measurement light belonging to a predetermined wavelength band toward a measurement region formed by at least a part of a living body;
detecting the measurement light emitted from a light source and transmitted through the living body by a plurality of sensors arranged regularly in a predetermined disposition, wherein each sensor of the plurality of sensors comprises a light reception region including a rectilinear light reception region that obtains a measurement of rectilinear light transmitted through the living body and a scattered light reception region that obtains a measurement of scattered light transmitted through the living body, the scattered light reception region being different from the rectilinear light reception region; and
analyzing rectilinearity of the measurement light in the living body and an optical distance from the light source using a detection result of the detected measurement light.

12. A non-transitory computer-readable recording medium having instructions recorded thereon, the instructions causing a computer in communication with a measurement module including a light source that emits at least one kind of measurement light belonging to a predetermined wavelength band toward a measurement region formed by at least a part of a living body and a detection unit in which a plurality of sensors are arranged regularly in a predetermined disposition wherein the measurement light emitted from the light source and transmitted through the living body is detected by the plurality of sensors, to execute a method comprising: analyzing rectilinearity of the measurement light in the living body and an optical distance from the light source using a detection result of the measurement light detected by the detection unit, wherein each sensor of the plurality of sensors comprises a light reception region including a rectilinear light reception region that obtains a measurement of rectilinear light transmitted through the living body and a scattered light reception region that obtains a measurement of scattered light transmitted through the living body, the scattered light reception region being different from the rectilinear light reception region.

* * * * *